(12) United States Patent
Bamdad

(10) Patent No.: US 7,585,682 B2
(45) Date of Patent: Sep. 8, 2009

(54) MAGNETIC IN SITU DILUTION

(75) Inventor: Cynthia C. Bamdad, Newton, MA (US)

(73) Assignee: Minerva Biotechologies Corporation, Waltham, MA (US)

( * ) Notice: Subject to any disclaimer, the term of this patent is extended or adjusted under 35 U.S.C. 154(b) by 1047 days.

(21) Appl. No.: 09/971,099

(22) Filed: Oct. 3, 2001

(65) Prior Publication Data

US 2002/0086443 A1 Jul. 4, 2002

Related U.S. Application Data

(60) Provisional application No. 60/237,427, filed on Oct. 3, 2000, provisional application No. 60/272,727, filed on Mar. 1, 2001.

(51) Int. Cl.
*G01N 33/553* (2006.01)
*B05D 5/12* (2006.01)

(52) U.S. Cl. .................. 436/526; 436/518; 436/149; 436/150; 436/151; 436/806; 436/94; 436/23.1; 436/24.3; 436/24.33; 436/25.3; 435/6; 435/287.1; 435/287.2; 435/287.3; 422/82.01; 427/10; 427/127; 427/128

(58) Field of Classification Search .......... 436/518, 436/526, 149, 150, 151, 806, 94, 23.1, 24.3, 436/24.33, 25.3; 435/6, 287.1, 287.2, 287.3; 422/82.01; 427/10, 127, 128
See application file for complete search history.

(56) References Cited

U.S. PATENT DOCUMENTS 4,791,069 A   12/1988  Hovorka et al.

5,411,863 A * 5/1995 Miltenyi .................. 435/6

(Continued)

FOREIGN PATENT DOCUMENTS

EP          0 142 301 A2     5/1985

(Continued)

OTHER PUBLICATIONS

Bain et al., "Formation of Monolayers by the Coadsorption of Thiols on Gold: Variation in the Head Group, Tail Group, and Solvent," *J. Am Chem. Soc.* 111, 7155-7164 (1989).

(Continued)

*Primary Examiner*—Mark L Shibuya
*Assistant Examiner*—Pensee T Do
(74) *Attorney, Agent, or Firm*—Joseph H. Kim; JHK Law

(57) ABSTRACT

The invention involves methods, assays, and components for the detection and analysis of binding between biological or chemical species, and can specifically be used for drug discovery. In an example where drug discovery is carried out, different candidate drugs can be attached to different articles such as magnetic beads. The beads can be exposed to colloid particles carrying signaling entities, or other signaling entities, immobilized with respect to protein targets of the drug candidates. After incubation, all beads are drawn to separate surface locations magnetically. Beads are released from surface locations where it is determined that signaling entities do not exist, and are removed from the assay. Beads held at other surface locations then are released, re-distributed, and re-attracted to surface locations. This is repeated with appropriate wash steps, until individual drug candidates can be isolated and identified.

19 Claims, 4 Drawing Sheets

U.S. PATENT DOCUMENTS

| | | | |
|---|---|---|---|
| 5,512,131 | A | 4/1996 | Kumar et al. |
| 5,620,820 | A | 4/1997 | Bertrand et al. |
| 5,620,850 | A | 4/1997 | Bamdad et al. |
| 5,981,297 | A * | 11/1999 | Baselt .................. 436/514 |
| 6,096,500 | A * | 8/2000 | Oprandy et al. ............ 435/6 |
| 6,100,045 | A * | 8/2000 | Van Es .................. 435/7.1 |
| 6,103,537 | A * | 8/2000 | Ullman et al. ........... 436/526 |
| 6,319,670 | B1 | 11/2001 | Sigal et al. |
| 6,355,591 | B1 * | 3/2002 | Kuvettu et al. ............ 502/68 |
| 6,409,925 | B1 * | 6/2002 | Gombinsky et al. ...... 210/695 |
| 6,455,325 | B1 * | 9/2002 | Tajima .................. 436/526 |
| 6,468,810 | B1 * | 10/2002 | Korpela ................. 436/526 |
| 6,541,617 | B1 * | 4/2003 | Bamdad et al. ......... 536/23.1 |
| 6,649,419 | B1 * | 11/2003 | Anderson ............... 436/526 |

FOREIGN PATENT DOCUMENTS

| | | | |
|---|---|---|---|
| WO | WO 96/29629 | A2 | 9/1996 |
| WO | WO 98/04740 | A1 | 2/1998 |
| WO | WO 99/38013 | A2 | 7/1999 |
| WO | WO 00/43783 | A2 | 7/2000 |
| WO | WO 00/43791 | A2 | 7/2000 |
| WO | WO 00/54882 | A1 | 9/2000 |
| WO | WO 00/63694 | A1 | 10/2000 |
| WO | WO 00/63701 | A2 | 10/2000 |
| WO | WO 01/51668 | A1 | 7/2001 |
| WO | WO 02/01225 | A2 | 1/2002 |
| WO | WO 02/01230 | A2 | 1/2002 |
| WO | WO 02/29411 | A2 | 4/2002 |
| WO | WO 02/37109 | A2 | 5/2002 |
| WO | WO 02/061129 | A2 | 8/2002 |
| WO | WO 03/018846 | A1 | 3/2003 |

OTHER PUBLICATIONS

Bain et al., "Formation of Monolayers by the Coadsorption of Thiols on Gold: Variation in the Length of the Alkyl Chain," *J. Am Chem. Soc.* 111, 7164-7175 (1989).

Bamdad, Cynthia, "The Use of Variable Density Self-Assembled Monolayers to Probe the Structure of a Target Molecule," *Biophysical Journal*, vol. 75, Oct. 1998, pp. 1989-1996.

Laibinis, P.E. et al., "Orthogonal Self-Assembled Monolayers: Alkanethiols on Gold and Alkane Carboxylic Acids on Alumina," *Science*, 245, 845-847 (1989).

Robinson, G.A., et al., "Bioelectrochemical Enzyme Immunoassay of Human Choriogonadotropin with Magnetic Electrodes," *Clin. Chem.* 31/9, (1985), pp. 1449-1452.

Search Report mailed Jun. 21, 2002 from International Patent Application No. PCT/US01/31061.

Written Opinion mailed Oct. 14, 2002 from International Patent Application No. PCT/US01/31061.

* cited by examiner

MAGNETIC IN SITU DILUTION

RELATED APPLICATIONS

This non-provisional application claims the benefit under Title 35, U.S.C. §119(e) of co-pending U.S. provisional application No. 60/237,427, filed Oct. 3, 2000 and U.S. provisional application No. 60/272,727, filed Mar. 1, 2001, each of which is incorporated by reference herein.

FIELD OF THE INVENTION

This invention relates to methods, assays, and components for the detection and analysis of binding between biological or chemical species, and can be used specifically for drug discovery.

BACKGROUND OF THE INVENTION

In certain areas of chemistry and biology the determination of binding interactions between molecules is of utmost importance. This is especially true in connection with studies involving physiology. A myriad of chemical and biochemical interactions associated with physiological processes, or with the interaction of chemicals with physiological processes, involve recognition of one molecular entity by another. One class of such interactions involves the physiological activity of pharmaceuticals (drugs). Precise understanding of the interaction of drugs with physiological entities, and the design of and/or discovery of drugs that can interact physiologically is, of course, of huge interest to society.

Drug discovery typically is facilitated by screening large numbers of candidate drugs for interaction with physiological targets such as target receptors or proteins. Known techniques for drug screening include studying candidate drugs individually for their pharmaceutical potential, often in parallel with tens, hundreds, or thousands of other drug candidates. In a typical process thousands of drug candidates (a library), each known to have at least some potential for some type of pharmaceutical use, are studied, in parallel, for their activity in connection with a specific physiological target. While this and other techniques for screening drugs, and studying other chemical or biological binding interactions are known, some are time-consuming and laborious. A need exists for improved, varied, and in some cases more rapid techniques for studying such interactions.

SUMMARY OF THE INVENTION

The present invention provides, generally, techniques for separating interacting components from a mixture of putative binding partners, determining the identity of an unknown analyte, determining which of a number of species binds to a known species, determining whether a species exists in a mixture that binds to another species, and/or a combination these and other techniques.

In one embodiment, the invention involves magnetically drawing a first article and a first chemical or biological agent immobilized relative to the first article to a first location, and drawing a second article to a second location. The first or second article is selectively released from its location while the other is held at its location.

In a further embodiment, a decision whether to release the first or second article can be made based upon whether the first or second article has captured a binding partner or analyte. Repeated magnetic drawing and releasing steps can result in isolation, from a series of putative binding partners, a single binding partner of an analyte.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
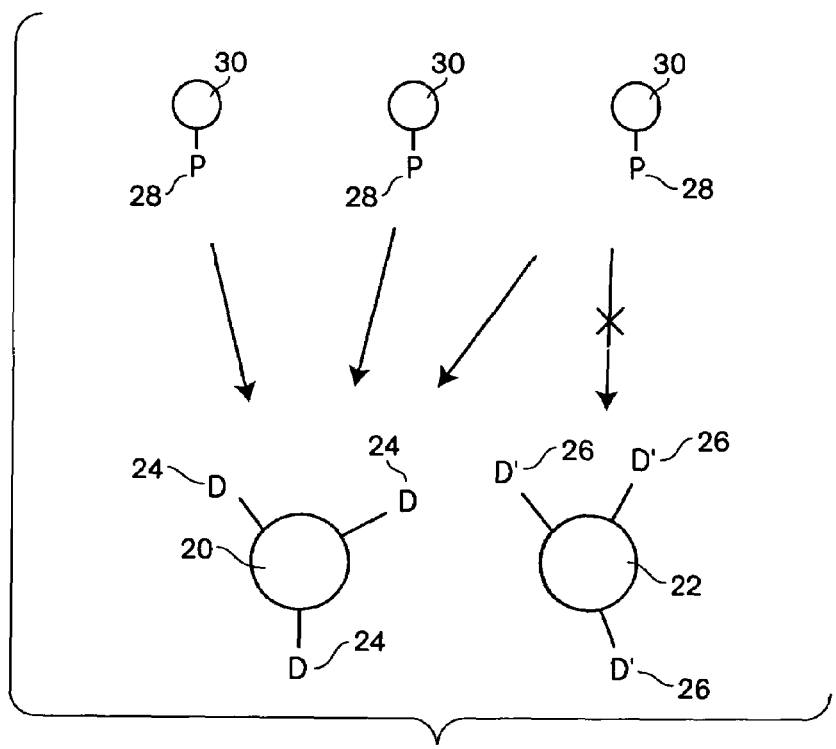
FIG. 1 illustrates schematically (as do the remaining figures) binding between colloid-immobilized proteins and a first magnetic-bead-immobilized drug candidate but not a second magnetic-bead-immobilized drug candidate.

International patent application serial number PCT/US00/01997, filed Jan. 25, 2000 by Bamdad et al., entitled "Rapid and Sensitive Detection of Aberrant Protein Aggregation in Neurodegenerative Diseases" (published as WO 00/43791 on Jul. 27, 2000), International patent application serial number PCT/US00/01504, filed Jan. 21, 2000 by Bamdad, et al, entitled "Interaction of Colloid-Immobilized Species with Species on Non-Colloidal Structures" (published as WO 00/43783 on Jul. 27, 2000), commonly-owned, copending U.S. patent application Ser. No. 09/602,778, filed Jun. 23, 2000 by Bamdad et al., entitled "Interaction of Colloid-Immobilized Species with Species on Non-Colloidal Structures"; and commonly-owned, copending U.S. patent application Ser. No. 09/631,818, filed Aug. 03, 2000 by Bamdad et al., entitled "Rapid and Sensitive Detection of Protein Aggregation" all are incorporated herein by reference.

Definitions

"Small molecule", as used herein, means a molecule less than 5 kiloDalton, more typically less than 1 kiloDalton. As used herein, "small molecule" excludes proteins.

The term "candidate drug" as used herein, refers to any medicinal substance used in humans, animals, or plants. Encompassed within this definition are compound analogs, naturally occurring, synthetic and recombinant pharmaceuticals, hormones, antimicrobials, neurotransmitters, etc. This includes any substance or precursor (whether naturally occurring, synthetic or recombinant) which is to be evaluated for use as a drug for treatment of neurodegenerative disease, or other disease characterized by aberrant aggregation, or prevention thereof. Evaluation typically takes place through activity in an assay, such as the screening assays of the present invention.

A variety of types of particles can be used in the invention. For example, "fluid suspendable particle" means a particle that can be made to stay in suspension in a fluid in which it is used for purposes of the invention (typically an aqueous solution) by itself, or can be maintained in solution by application of a magnetic field, an electromagnetic field, agitation such as stirring, shaking, vibrating, sonicating, centrifuging, vortexing, or the like. A "magnetically suspendable" particle is one that can be maintained in suspension in a fluid via application of a magnetic field. An electromagnetically-suspendable particle is one that can be maintained in suspension in a fluid by application of an electromagnetic field (e.g., a particle carrying a charge, or a particle modified to carry a charge). A "self-suspendable particle" is a particle that is of low enough size and/or mass that it will remain in suspension in a fluid in which it is used (typically an aqueous solution), without assistance of, for example, a magnetic field, for at least 1 hour. Other self-suspendable particles will remain in suspension, without assistance, for 5 hours, 1 day, 1 week, or even 1 month, in accordance with the invention.

"Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids.

As used herein, a "metal binding tag" refers to a group of molecules that can become fastened to a metal that is coordinated by a chelate. Suitable groups of such molecules include amino acid sequences, typically from about 2 to about 10 amino acid residues. These include, but are not limited to, histidines and cysteines ("polyamino acid tags"). Such binding tags, when they include histidine, can be referred to as a "polyhistidine tract" or "histidine tag" or "HIS-tag", and can be present at either the amino- or carboxy-terminus, or at any exposed region, of a peptide or protein or nucleic acid. A poly-histidine tract of six to ten residues is preferred for use in the invention. The polyhistidine tract is also defined functionally as being a number of consecutive histidine residues added to a protein of interest which allows the affinity purification of the resulting protein on a metal chelate column, or the identification of a protein terminus through the interaction with another molecule (e.g. an antibody reactive with the HIS-tag).

"Affinity tag" is given its ordinary meaning in the art. Affinity tags include, for example, metal binding tags, GST (in GST/glutathione binding clip), and streptavidin (in biotin/streptavidin binding). At various locations herein specific affinity tags are described in connection with binding interactions. It is to be understood that the invention involves, in any embodiment employing an affinity tag, a series of individual embodiments each involving selection of any of the affinity tags described herein.

As used herein, "chelate coordinating a metal" or metal coordinated by a chelate, refers to a metal coordinated by a chelating agent that does not fill all available coordination sites on the metal, leaving some coordination sites available for binding via a metal binding tag.

As used herein, "metal binding tag/metal/chelate linkage" defines a linkage between first and second species in which a first species is immobilized relative to a metal binding tag and a second species is immobilized relative to a chelate, where the chelate coordinates a metal to which the metal binding tag is also coordinated. U.S. Pat. No. 5,620,850 of Bamdad, et al., incorporated herein by reference, describes exemplary linkages.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily detected visibly (unaided or with a microscope including an electron microscope or the like), or spectroscopically, entities that can be detected electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horse radish peroxidase and alkaline phosphatase. "Precursors of signaling entities" are entities that by themselves may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein. As used herein, "fastened to or adapted to be fastened", in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is covalently attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) which molecule also presents a chelate coordinating a metal. A species also is adapted to be fastened to a surface if a surface carries a particular nucleotide sequence, and the species includes a complementary nucleotide sequence.

"Covalently fastened" means fastened via nothing other than one or more covalent bonds. E.g. a species that is covalently coupled, via EDC/NHS chemistry, to a carboxylate-presenting alkyl thiol which is in turn fastened to a gold surface, is covalently fastened to that surface.

"Specifically fastened" or "adapted to be specifically fastened" means a species is chemically or biochemically linked to a surface as described above with respect to the definition of "fastened to or adapted to be fastened", but excluding all non-specific binding.

"Non-specific binding", as used herein, is given its ordinary meaning in the field of biochemistry.

"Colloids", as used herein, means nanoparticles, i.e. very small, self-suspendable or fluid-suspendable particles including those made of material that is, e.g., inorganic or organic, polymeric, ceramic, semiconductor, metallic (e.g. gold), non-metallic, crystalline, amorphous, or a combination. Typically, colloid particles used in accordance with the invention are of less than 250 nm cross section in any dimension, more typically less than 100 nm cross section in any dimension, and in most cases are of about 2-30 nm cross section. One class of colloids suitable for use in the invention is 10-30 nm in cross section, and another about 2-10 nm in cross section. As used herein this term includes the definition commonly used in the field of biochemistry.

A "moiety that can coordinate a metal", a used herein, means any molecule that can occupy at least two coordination sites on a metal atom, such as a metal binding tag or a chelate.

As used herein, a component that is "immobilized relative to" another component either is fastened to the other component or is indirectly fastened to the other component, e.g., by being fastened to a third component to which the other component also is fastened, or otherwise is translationally associated with the other component. For example, a signaling entity is immobilized with respect to a binding species if the signaling entity is fastened to the binding species, is fastened to a colloid particle to which the binding species is fastened, is fastened to a dendrimer or polymer to which the binding species is fastened, etc.

"Diverse biological species" means different animals, such as mouse and hamster, mouse and goat, etc.

The term "sample" refers to any cell, tissue, or fluid from a biological source (a "biological sample", or any other medium, biological or non-biological, that can advantageously be evaluated in accordance with the invention including, but not limited to, a biological sample drawn from a human patient, a sample drawn from an animal, a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to whom a candidate drug has been given to determine the efficacy of the drug.

A "sample suspected of containing" a particular component means a sample with respect to which the content of the component is unknown. For example, a fluid sample from a human suspected of having a disease, such as a neurodegenerative disease or a non-neurodegenerative disease, but not known to have the disease, defines a sample suspected of containing neurodegenerative disease aggregate-forming species. "Sample" in this context includes naturally-occurring samples, such as physiological samples from humans or other animals, samples from food, livestock feed, etc., as well as "structurally predetermined samples", which are defined herein to mean samples, the chemical or biological sequence or structure of which is a predetermined structure used in an assay designed to test whether the structure is associated with a particular process such as a neurodegenerative disease. For example, a "structurally predetermined sample" includes a peptide sequence, random peptide sequence in a phage display library, and the like. Typical samples taken from humans or other animals include cells, blood, urine, ocular fluid, saliva, cerebro-spinal fluid, fluid or other samples from tonsils, lymph nodes, needle biopsies, etc.

"Molecular wires" as used herein, means wires that enhance the ability for a fluid encountering a SAM-coated electrode to communicate electrically with the electrode. This includes conductive molecules or, as mentioned above and exemplified more fully below, molecules that can cause defects in the SAM allowing communication with the electrode. A non-limiting list of additional molecular wires includes 2-mercaptopyridine, 2-mercaptobenzothiazole, dithiothreitol, 1, 2-benzenedithiol, 1, 2-benzenedimethanethiol, benzene-ethanethiol, and 2-mercaptoethylether. Conductivity of a monolayer can also be enhanced by the addition of molecules that promote conductivity in the plane of the electrode. Conducting SAMs can be composed of, but are not limited to: 1) poly (ethynylphenyl) chains terminated with a sulfur; 2) an alkyl thiol terminated with a benzene ring; 3) an alkyl thiol terminated with a DNA base; 4) any sulfur terminated species that packs poorly into a monolayer; 5) all of the above plus or minus alkyl thiol spacer molecules terminated with either ethylene glycol units or methyl groups to inhibit non specific adsorption. Thiols are described because of their affinity for gold in ready formation of a SAM. Other molecules can be substituted for thiols as known in the art from U.S. Pat. No. 5,620,820, and other references. Molecular wires typically, because of their bulk or other conformation, creates defects in an otherwise relatively tightly-packed SAM to prevent the SAM from tightly sealing the surface against fluids to which it is exposed. The molecular wire causes disruption of the tightly-packed self-assembled structure, thereby defining defects that allow fluid to which the surface is exposed to communicate electrically with the surface. In this context, the fluid communicates electrically with the surface by contacting the surface or coming in close enough proximity to the surface that electronic communication via tunneling or the like, can occur.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo binding with a particular molecule. Biological binding partners are examples. For example, Protein A is a binding partner of the biological molecule IgG, and vice versa. .

The term "determining" refers to quantitative or qualitative analysis of a species via, for example, spectroscopy, ellipsometry, piezoelectric measurement, immunoassay, electrochemical measurement, and the like. "Determining" also means detecting or quantifying interaction between species, e.g. detection of binding between two species.

The term "self-assembled monolayer" (SAM) refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis, P. E.; Hickman, J.; Wrighton, M. S.; Whitesides, G. M. *Science* 245, 845 (1989), Bain, C.; Evall, J.; Whitesides, G. M. *J. Am. Chem. Soc.* 111, 7155-7164 (1989), Bain, C.; Whitesides, G. M. *J. Am. Chem. Soc.* 111, 7164-7175 (1989), each of which is incorporated herein by reference.

The term "self-assembled mixed monolayer" refers to a heterogeneous self-assembled monolayer, that is, one made up of a relatively ordered assembly of at least two different molecules.

The present invention provides techniques, kits, and articles for determination of binding between chemical or biological species, especially for determining which, of a series of species, bind to a particular target species and which do not. Techniques of the invention are useful for determination of essentially any binding interactions, typically biological binding interactions.

Certain embodiments of the invention make use of self-assembled monolayers (SAMs) on surfaces, such as surfaces of colloid particles, and articles such as colloid particles having surfaces coated with SAMs. In one set of preferred embodiments, SAMs formed completely of synthetic molecules completely cover a surface or a region of a surface, e.g. completely cover the surface of a colloid particle. "Synthetic molecule", in this context, means a molecule that is not naturally occurring, rather, one synthesized under the direction of human or human-created or human-directed control. "Completely cover" in this context, means that there is no portion of the surface or region that directly contacts a protein, antibody, or other species that prevents complete, direct coverage with the SAM. I.e. the surface or region includes, across its entirety, a SAM consisting completely of non-naturally-occurring molecules (i.e. synthetic molecules). The SAM can be made up completely of SAM-forming species that form close-packed SAMs at surfaces, these species in combination with molecular wires or other species able to promote electronic communication through the SAM (including defect-promoting species able to participate in a SAM), other species able to participate in a SAM, and any combination of these. Preferably, all of the species that participate in the SAM include a functionality that binds, optionally covalently, to the surface, such as a thiol which will bind to a gold surface covalently. A self-assembled monolayer on a surface, in accordance with the invention, can be comprised of a mixture of species (e.g. thiol species when gold is the surface) that can present (expose) essentially any chemical or biological functionality. For example, they can include tri-ethylene glycol-terminated species (e.g. tri-ethylene glycol-terminated thiols) to resist non-specific adsorption, and other species (e.g. thiols) terminating in a binding partner of an affinity tag, e.g. terminating in a chelate that can coordinate a metal such as nitrilotriacetic acid which, when in complex with nickel atoms, captures histidine-tagged binding species. These arrangements can be used for a variety of embodiments of the invention. As an example, a self-assembled monolayer, whether formed on a colloid or on another surface, can be comprised of a mixture of thiol species (when gold is the surface) that include triethylene glycol-terminated thiols to resist non-specific adsorption and thiols terminating in a binding partner of an affinity tag, e.g. terminating in a chelate that can coordinate a metal such as nitrilo tri-acetic acid which, when in complex with nickel atoms, capture histidine-tagged binding species. In a preferred embodiment the binding species is a beta-amyloid peptide which can readily self-aggregate. The present invention provides a method for rigorously controlling the concentration of the histidine-tagged peptides presented on the colloid surface. Without this rigorous control over peptide density on each colloid particle, co-immobilized peptides would readily aggregate with each other to form micro-hydrophobic-domains that would catalyze colloid-colloid aggregation in the absence of aggregate-forming species present in a sample. This is an advantage of the present invention, over existing colloid agglutination assays.

The methods described in the present invention produce self-assembled monolayers on colloids that resist non-specific adsorption without protein blocking steps, such as blocking with BSA. The methods described herein also produce derivatized colloids that are stable in biologically relevant fluids and do not require detergents (for stability; maintaining colloids in suspension), which interfere with binding reactions. This allows sensitive binding assays to be performed in solution. This abrogates the need for having binding partners adhered to adsorbent surfaces, as is common for existing colloid agglutination assays. As is discussed below, detergent can advantageously be used for SAM formation on colloids. In this case, detergent can be and preferably is removed after SAM formation and is no longer present on the colloid, in the SAM, or elsewhere during binding interactions or other use of the colloids.

A target molecule can be attached to an electronic signaling colloid and then incubated with magnetic beads that each present a separate drug candidate species. Following incubation, the magnetic beads can be magnetically attracted to a sensing electrode and analyzed by, for example, ACV. An interaction between a drug on a magnetic bead and a target molecule on an electronic signaling colloid renders the resultant complex both recruitable and detectable. Complexes are magnetically attracted to an electrode and electronically analyzed. Various techniques for producing SAMs on colloids and assays involving beads and colloidal particles are described in International Patent Application PCT/US00/01997, filed Jan. 25, 2000, entitled "Rapid and Sensitive Detection of Aberrant Protein Aggregation in Neurodegenerative Diseases," by Bamdad, et al., published Jul. 27, 2000 as WO 00/43791 and in International Patent Application PCT/US00/01504, filed Jan. 21, 2000, entitled "Assays Involving Colloids and Non-Colloidal Structures," by Bamdad, et al., published Jul. 27, 2000 as WO 00/43783.

Small molecule drug libraries contain millions of discrete compounds, which poses a logistical challenge. Current practice is to pool drug candidates, test, analyze the individual components of pools that registered a positive, and repeat until a single interacting species has been identified. This practice is very time consuming. Another approach is to modify each drug candidate with a unique tag that codes for its identity and a fluorescent label. Target molecules, immobilized on polystyrene beads, are incubated with pooled drug candidates, then rinsed. The polystyrene beads that captured a drug candidate fluoresce and can be microscopically separated from the others. The captured drugs are then decoded to identify the small molecule that interacted. The problem with this approach is that the many labels that have been added to the drug candidates participate in the interactions, leading to many false positives.

An alternate approach is to synthesize drugs on, or attach to, magnetic beads. The encoding label is then attached to the bead not the drug candidate. Pools of drug-presenting magnetic beads are then mixed with colloids that present both the target molecule and an electronic label (such as a ferrocene-thiol incorporated into a SAM on the colloid). The solution is retained over an array of microelectrodes. A magnetic field can be separately applied to each electrode pad of the array. First, magnetic fields are applied to each electrode in the array to attract the magnetic beads. The array is then electronically analyzed (ACV preferred). Pads that register a positive, indicate that, at that address, a drug candidate on a magnetic bead has captured a target molecule on a signaling colloid. The magnetic field at spatial addresses that registered a positive remain "turned on", while the other magnetic fields are released, and an exit valve is opened to wash away magnetic beads bearing drug candidates that did not interact. The exit valve is closed and more solution is added to dilute the drug candidates in situ. The process is repeated several times to ensure that each positive results from a single magnetic bead, which bears a single drug candidate. These positives are collected and analyzed to identify the interacting drug candidates. Beads that bear drug candidates can be encoded or drugs can be released from the beads and submitted to analysis techniques such as mass spec, NMR, sequencing and the like.

Referring now to the figures, one technique for determination of binding interactions will be described. FIG. 1 illustrates, schematically, first and second articles 20 and 22, respectively. Articles 20 and 22 can be any articles that can immobilize a chemical or biological species for binding study, and can be drawn magnetically from one place to another via a magnetic field. Polymeric magnetic beads that are typically used in biochemical analyses are convenient to use for articles 20 and 22, and the articles will be referred to as magnetic beads hereinafter with the understanding that other articles can be used.

Magnetic bead 20 carries a first chemical or biological agent 24 (D) immobilized relative to the bead, and magnetic bead 22 similarly carries an immobilized second chemical or biological agent 26 (D').

In FIG. 1 binding partners 28 (P) also are provided, each immobilized relative to a signaling entity 30. As illustrated, signaling entity 30 is a colloid particle. In the embodiment illustrated, binding partner 28 has binding affinity for first chemical or biological agent 24, but not for second biological or chemical agent 26. Accordingly, exposure of all components illustrated in FIG. 1 to each other, for example via mixing in a typically biochemical assay fluid medium, will result in binding of binding partner 28 to first agent 24, and corresponding immobilization of bead 20 relative to signaling entity 30. Signaling entity 30 does not become immobilized relative to bead 22.

A variety of signaling entities can be immobilized relative to surfaces of a variety of articles, such as colloid particles, if desired. Signaling entities such as fluorescent-conjugated antibodies and other fluorescent fusion proteins, including green fluorescent proteins, can easily be attached to surfaces of gold colloids and other surfaces that also present putative binding partners either through affinity tags, EDC/NHS chemistry or by binding to a His-tagged protein A or G presented on NTA-SAM-coated colloids according to the invention. Signaling entities such as fluorescent moieties also can be co-immobilized on a colloid via a biotin terminated ligand, or may be fastened via a chelate/metal/metal binding tag linkage. A fluorescent moiety may also be fastened by attaching it to an antibody and using a chelate/metal/metal binding tag with His-protein G to bind the antibody. The moieties can then be directly detected. In a preferred embodiment, the signaling entity is electroactive, specifically a redox-active complex, which can be electrochemically detected by, for example, alternating current voltammetry (ACV).

Although any of a variety of binding interactions can be studied in accordance with the invention, a preferred technique involves high-throughput detection of drug candidate/target molecule interactions. In such an arrangement, first and second agents 24 and 26 (D and D' respectively) are drug candidates and binding partner 28 is a target protein that may bind to one drug candidate but may not bind to other drug candidates. This specific assay will be discussed with respect to the remainder of the figures, but it is to be understood that the invention is not limited to drug candidate/target protein interactions.

In a typical drug screening assay, a very large number (from thousands to millions) of drug candidates can be provided, immobilized with respect to magnetic beads. Preferably, each magnetic bead carries only one type of immobilized drug candidate, and there may be only one bead per drug candidate provided, or many beads per drug candidate. One advantage of the invention, as will become more fully understood from the description below, is that only one bead need be provided for each drug candidate. That is, a plurality of beads can be provided in an assay, for each bead carries a different immobilized drug candidate.

In the figures, signaling entity 30 is shown as a colloid particle, and use of a colloid particle as a signaling entity, or as a structure for assistance in the immobilization of a different signaling entity (described below) with respect to target protein 28, is preferred. In particular, colloid particles exposing gold surfaces, such as gold colloid particles, are particularly convenient. Although colloid particles will be discussed in connection with protein 28 hereinafter, it is understood that the protein, or other binding partner, can be immobilized with respect to a signaling entity without use of a colloid particle.

Immobilization of drug candidates 24 and 26 to magnetic beads 20 and 22 can be carried out by any technique known in the art. Such techniques are routine. Drug candidates should be presented at the surfaces of the magnetic beads in a concentration sufficient to facilitate adequate binding and signaling, which can be easily tailored by those of ordinary skill in the art with the knowledge of requirements of assays of the invention.

Binding partners 28 can be immobilized relative to colloid particles 30 via thiol linkage. That is, binding partners 28 can incorporate a thiol, or can be chemically attached or otherwise immobilized to a thiol, which will bind to a gold surface of colloid particles 30. In one preferred embodiment proteins 28 are attached to self-assembled monolayers (SAMs) formed on surfaces of gold colloid particles 30 via a metal binding tag/metal/chelate linkage. In such a case a metal binding tag can be attached to binding partner 28, and the colloid can carry a SAM presenting a chelate coordinating a metal to which the binding tag binds. Other affinity tags can be used to attach binding partners 28 to SAM species on the colloid particles. In another embodiment SAMs on colloid particles present carboxylate groups, and binding partners 28 incorporate or are immobilized relative to primary amines which can be linked to the SAMs via EDC/NHS chemistry. Affinity tag/binding partner linkage, or EDC/NHS chemistry can be used to link essentially any species to essentially surface of the invention. Preferably such SAMs include sufficient exposure of protein 28 to facilitate binding to drug candidate 24, the remainder of the self-assembled monolayer comprising non-specific binding-inhibiting species such as polyethylene-glycol-terminated SAM-forming species. The selective attachment of various species to self-assembled monolayer-forming species, to form self-assembled monolayers at surfaces exposing desired chemical or biochemical functionality, are known from references noted above and additional documents including U.S. Pat. No. 5,512,131 and International Patent Publication WO 96/29629, published Jun. 26, 1996, each of which is incorporated herein by reference. Chemistry for attachment of proteins 28 to colloid particles 38 also is described in co-pending, commonly owned International Patent Application Serial No. PCT/US00/01504 of Bamdad and Bamdad, filed Jan. 21, 2000, published as WO 00/43783 on Jul. 27, 2000 and incorporated herein by reference.

In another technique, SAMs can be formed on colloid particles 30 that incorporate carboxy-terminated thiols. EDC/NHS coupling chemistry then can be used to attach any molecule that presents a primary amine to the SAM. Most proteins 28 will include primary amines, and attachment of primary amines to molecules for subsequent attachment to SAMs on colloid particle 30 is thereby facilitated. Typical EDC/NHS linkage can be carried out as follows.

A dimethyl formamide (DMF) solution containing 20-40 micromolar NTA (nitrilotriacetic acid) C11 thiol, 540-580 micromolar COOH—C11 thiol and +/−40 micromolar ferrocenyl-C11 thiol is prepared. Colloid particles are incubated in the solution. Following incubation, the DMF solution is removed, and the colloid particles are introduced into a second DMF solution containing 400 micromolar polyethylene glycol C11 thiol and heat cycled as described above. 30 microliters of the colloids are pelleted and resuspended in 100 microliters of phosphate buffer. To the buffer solution is added 0.5 micromoles N-ethyl-N' (3-dimethyl aminopropyl) carbodimide (EDC), and 0.1 micromoles of N-hydroxy succinimide plus a primary-amine-containing binding partner 28 to be linked to the colloids. The colloid solution plus binding partner is incubated for 10 minutes, during which time the binding partner attaches to the SAMs on the colloids. Removal of the solution, followed by washing and re-suspension followed. To avoid linkage of binding partner to more than one colloid particle, the volume of the solution in which the reaction occurs can be doubled or tripled appropriately. The binding partner can be demonstrated to be immobilized with respect to the colloids by exposure to agarose beads carrying a target immobilized thereto, and observing agglomeration.

Figure 2:
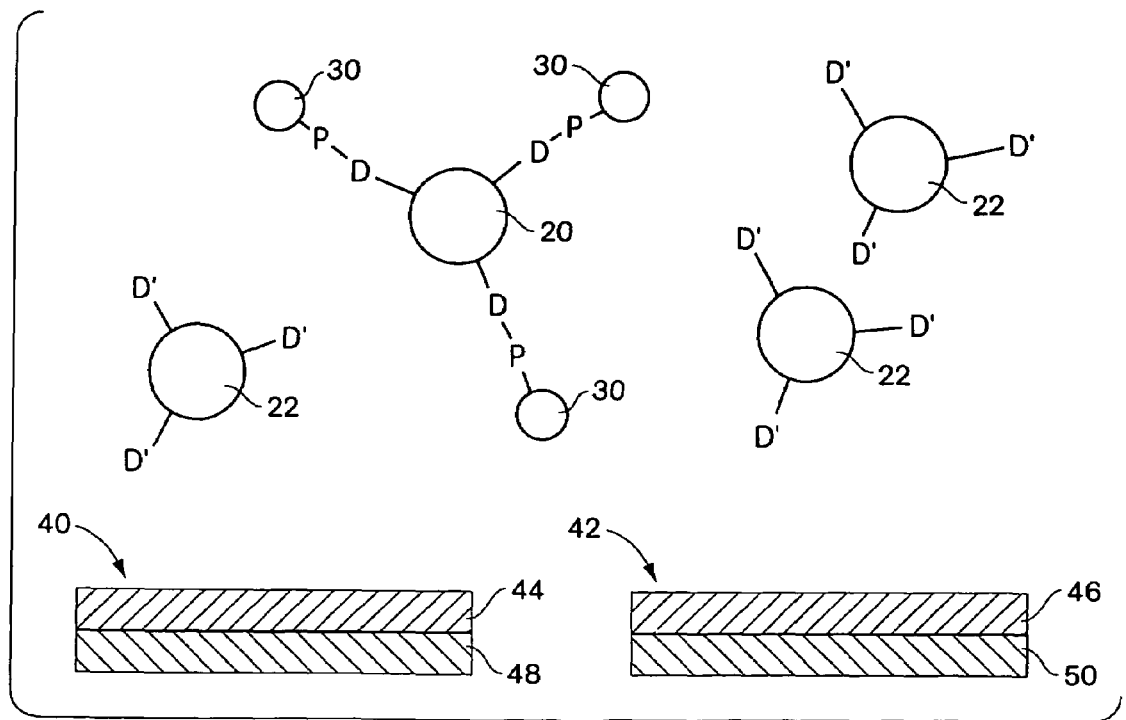
FIG. 2 illustrates a first drug candidate, immobilized relative to a magnetic bead and bound to colloid-immobilized proteins, and a second drug candidate, also immobilized to magnetic beads but not bound to colloid-immobilized proteins, in a mixture in the vicinity of magnetically-equipped electrodes.

In FIG. 2, the components illustrated in FIG. 1 are shown suspended in a fluid medium following binding of protein 28 to drug candidate 24. The components are suspended in the vicinity of a first location 40 and a second location 42, to which magnetic particles 20 and 22 can be magnetically drawn. Locations 40 and 42 can be predetermined areas of a surface of a single article, or surfaces of different articles. Whether locations 40 and 42 are of the same or of a different article is not important in connection with the invention, so long as the locations are separate and distinguishable to the extent that immobilization of a signaling entity at one location is distinguishable from immobilization at another location (as will become apparent from the description below). In a preferred embodiment, first and second locations 40 and 42 are surfaces of first and second electrodes 44 and 46, respectively, wherein an electromagnet is associated with each of the electrodes. Electromagnets can be positioned to draw beads 20 and 22 to the vicinity of the first and second locations 40 and 42. As illustrated, electromagnets 48 and 50 are shown in association with each of electrodes 44 and 46, respectively, and are positioned behind the electrodes with respect to components of the assay. Electrical circuitry addressing the electrodes and electromagnets is conventional, and is not shown.

Figure 3:
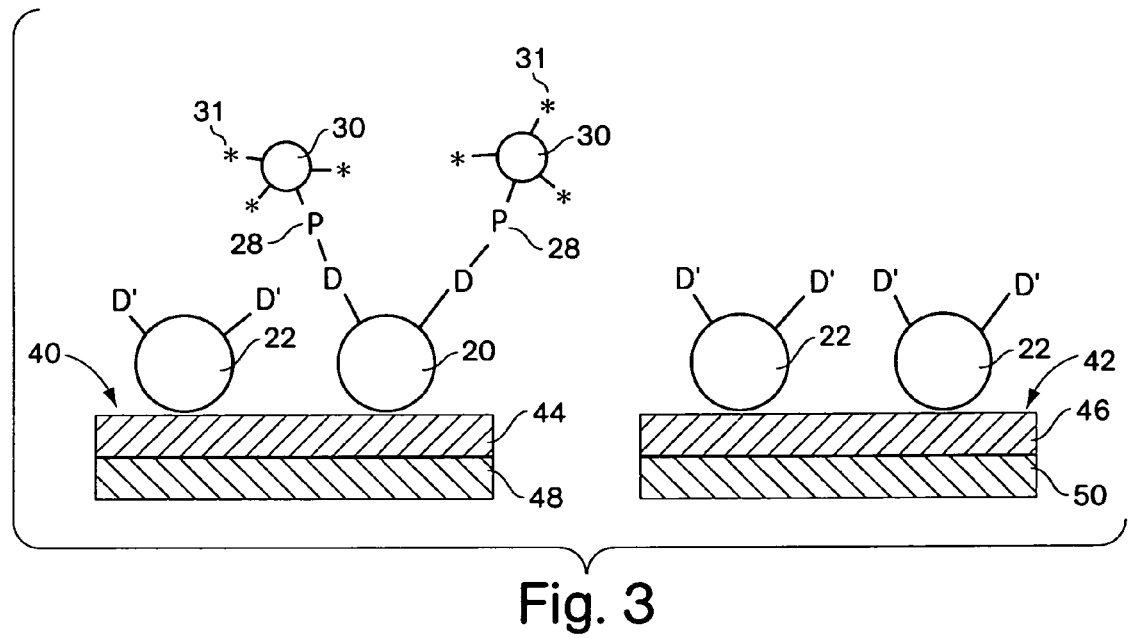
FIG. 3 illustrates the magnetic beads of FIG. 2, and components immobilized thereto, drawn to the surfaces of magnetically-equipped electrodes.
Figure 4:
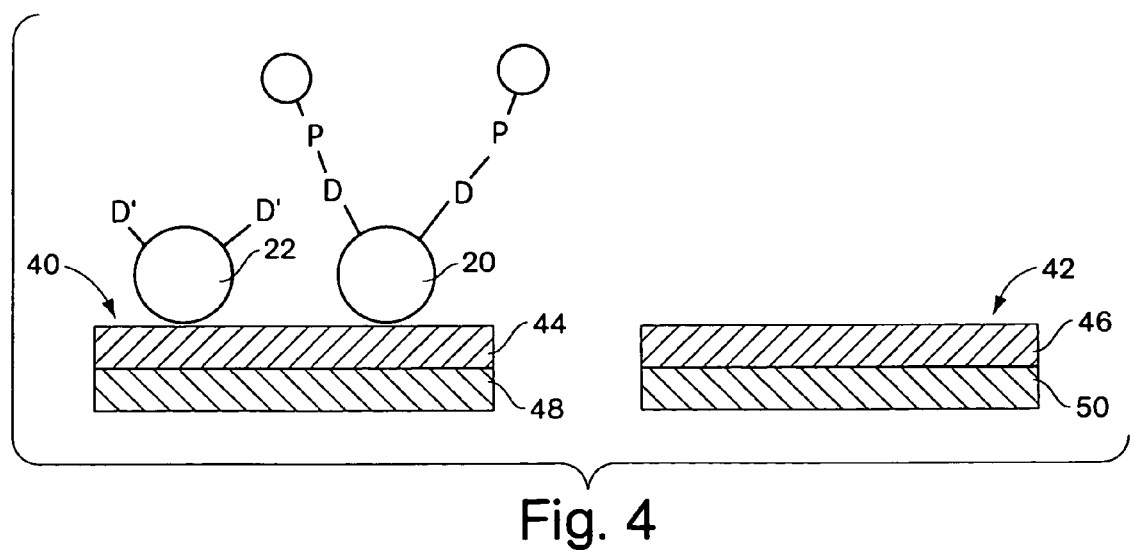
FIG. 4 illustrates the arrangement of FIG. 3 after selective deactivation of magnetic force associated with one electrode.

Magnetic beads 20 and 22 are magnetically drawn to first and second locations 40 and 42 by activation of electromagnets 48 and 50. Typically, beads 20 and 22 are carried in a fluid medium, such as an aqueous solution to which surface areas 40 and 42 are exposed. FIG. 3 illustrates beads 20 and 22, and species immobilized relative thereto, drawn to surface locations 40 and 42. The beads need be drawn within proximity to the surface locations only to the extent that the identification of signaling entities immobilized with respect to bead 20 can be identified. In one embodiment, signaling entities 30 are visibly identifiable. In this embodiment signaling entities 30 can be colloid particles (the aggregation proximate the surface of bead 20 will cause the bead to exhibit a blue or purple color distinguishable from other beads), can be fluorescent moieties, fluorescent particles or the like. In such a case, electrodes 44 and 46 are not required; it is only required that the beads be drawn magnetically to separate locations. When this has occurred, surface location 40 is identified as one that has attracted signaling entity 30, and location 42 as identified as one that has not attracted a signaling entity 30.

In another embodiment, the signaling entity comprises an electroactive molecule such as a redox-active species, the presence of which in proximity to electrode 44, and the absence of which in proximity to electrode 46, can be determined via known electrochemical techniques such as CV and ACV. Such electroactive molecules typically are metal-containing redox-active molecules including transition metal complexes, i.e., complexes including metals selected from, but not limited to, cadmium, copper, cobalt, palladium, zinc, iron, ruthenium, rhodium, osmium, rhenium, platinum, scandium, titanium, vanadium, chromium, manganese, nickel, molybdenum, technetium, tungsten, and iridium. Particularly preferred are ruthenium, osmium, iron, platinum, and palladium, with ruthenium and iron being especially preferred. Complexes including these metals will include the metals along with ligands such as, for example, isonicotinamide, imidazole, bipyridine, terpyridine, phenanthrolines, carbon monoxide, isocyanide, and metallocene ligands, including substituted derivatives of the above. Other ligands will be apparent to those of ordinary skill in the art. A particularly preferred metal complex of the invention is a metallocene complex, especially ferrocene, which includes an iron atom and two cyclopentadiene ligands, or a derivative thereof.

The signaling entity (31, first illustrated in FIG. 3 but optionally present in other figures) immobilized with respect to protein 28 can be fastened to a common colloid particle 30 to which protein 28 is itself fastened. This can be accomplished by forming a mixed SAM on colloid particle 30 including protein 28, the signaling entity (optionally electroactive such as ferrocene) and, optionally, non-specific-binding-inhibiting SAM-forming species. Where an electroactive signaling entity 31 is used, its proximity, or lack thereof, to locations 40 and 42 can easily be determined by those of ordinary skill in the art with electrodes 44 and 46 using known electrochemical techniques such as CV or ACV, as mentioned.

Figure 5:
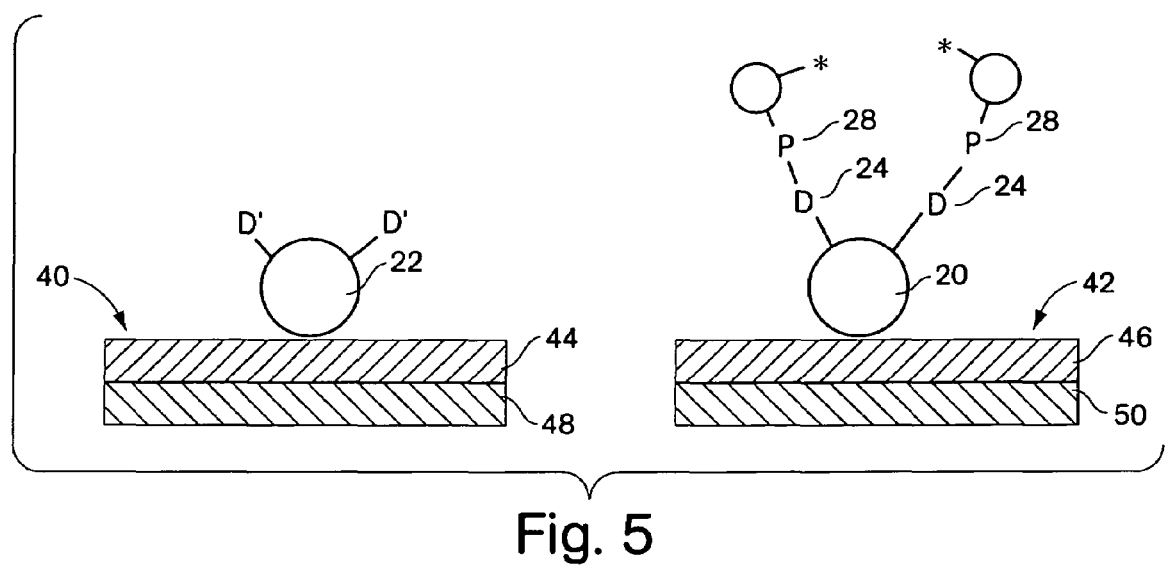
FIG. 5 illustrates the arrangement of FIG. 4 following deactivation of magnetic force associated with the remaining electrode and reactivation of magnetic force associated with both electrodes.

No matter which signaling technique is used, once it is determined that a signaling entity is present proximate location 40 but not present proximate location 42, electromagnet 50 is de-activated, and beads that had been drawn proximate location 42 are selectively released while beads proximate location 40 are retained in place magnetically. Following release of beads from location 42, at least location 42, and optionally locations 42 and 40, are rinsed to remove all beads not magnetically retained at location 40. Then, a fluid that preferably does not contain beads is introduced into the environment of surface locations 40 and 42, beads 20 and 22 are released from surface location 40 and suspended in the fluid, and the steps of magnetically drawing beads to surface locations, determining locations at which signaling entities are present, and releasing beads from surface locations where signaling entities are not present is repeated. Specifically, following the release of beads 20 and 22 from surface areas 40 electromagnets 48 and 50 are re-activated. Ideally, beads 20 and 22 will then be drawn to different surface locations, effectively separating them from each other (as shown in FIG. 5; repetition of the assay will result in such separation eventually). If bead 20 is drawn to surface location 42 (identified by the signaling entity), then electromagnet 48 can be deactivated, releasing bead 22 which can be removed by rinsing, with only bead 20 remaining immobilized to a surface location. Drug candidate 24 then can be identified as one that has binding affinity for target protein 28. This can be accomplished by any of a variety of known techniques. In one technique, each bead is tagged with a unique radiolabel which is read to reveal the chemical history of its attached candidate drug. Other labeling schemes involving nucleic acid or peptide labeling of each synthetic step are possible. Another approach involves cleaving candidate drug 24 from bead 20 and analyzing it using a technique such as mass spectrometry.

As illustrated in FIGS. 1-5, only two types of beads (20 and 22), carrying only two types of candidate drugs (D and D'), are shown. In an actual assay hundreds, thousands, or millions of beads, each carrying a unique drug, are used. Beads carrying drug candidates are readily available or preparable by those of ordinary skill in the art, for example, using combinatorial synthesis, solid phase synthesis approaches, or postsynthetic attachment. In a typical high-volume screening technique it may be desirable to screen, e.g., ten million drugs (D, D', D", . . . ) against interaction with a binding partner. In conventional technology this would typically involve ten million experiments, or parallel screening (for example on multiwell plates) of ten million drugs, a time-consuming and laborious process. In the present invention, however, a much smaller number of surface locations (40, 42, . . . ) need be employed than the number of drug candidates screened. The size of the surface areas, and their number, is selected such that many beads (20, 22, . . . ) presenting many drug species are drawn to a single surface location. In a typical assay only one, or only a few of these beads will be immobilized with respect to signaling entities. Thus, the number of surface locations can be chosen, in conjunction with the number of beads and drug candidates and the number of expected positive binding interactions, such that in the first step of drawing the beads to separate surface locations at least some of the surface locations (generally many or most surface locations) will not exhibit the presence of a signaling entity. Once certain locations are identified as not attracting signaling entities, all beads from those locations can be released and rinsed away, and beads that are held at surface locations (surface locations exhibiting signaling entities; now a much smaller number) can be released, redistributed, redrawn to surface areas, and the assay repeated until only one magnetic bead, statistically, is present at each surface location. At that point, beads carrying signaling entities can be isolated from all other beads and the identity of their immobilized drug candidates determined.

The techniques of the invention allow for a reduction in labor in screening large numbers of possible binding interactions. For example, the screening of ten million drug candidates against a single potential binding protein can be carried out using ten thousand surface locations, or much fewer, for example only one thousand locations, or even one hundred surface locations or less. Of course, a drug library can alternatively be simultaneously screened for interaction with a panel of proteins. In this case, hetero-particle complexes may be subsequently analyzed to determine the identity of not only the drug, but also the protein to which it binds.

This advantage (efficient screening) of the invention defines one aspect of the invention which involves providing a plurality of binding partner candidates, such as drug candidates, each immobilized relative to separate articles, and studying binding of the binding partner candidates with a target immobilized with respect to a signaling entity and, in a process involving one tenth the number of surface locations relative to the number of binding partner candidates, determining, specifically, binding between at least one binding partner candidate and the target.

In another aspect of the invention, magnetic beads can be modified to present proteinaceous molecules, then tested according to methods of the invention for their ability to interact with (a) target species, which may also be proteinaceous, attached to a population of gold colloids. A complex sample mixture such as a cell lysate or a natural products sample can be fractionated, then fractions containing a single or a few distinct molecular species can be attached to magnetic beads. Attachment to magnetic beads can be facilitated by non-specific adsorption, or chemical coupling to functionalized beads. These beads may or may not be gold coated to facilitate the formation of SAMs on their surfaces. Using methods of the invention, a small number of beads are identified that present species that interact with colloid-immobilized target molecules. Interacting species can then be desorbed or cleaved from the particles and identified using standard biochemical analysis techniques, such as mass spectroscopy (MS) or matrix laser desorbtion ionization (MALDI) MS, or peptide sequencing techniques. Proteins that have been attached to magnetic beads via interaction with an affinity tag can be released for analysis by competitive inhibition of the interaction with the affinity tag. For example, magnetic beads bearing NTA-Ni moieties selectively capture histidine tagged species. The His-tagged species can be released from the bead by competitively inhibiting the interaction with added imidazole.

Alternatively, small numbers of distinct molecular species, from complex mixtures, can be attached to magnetic beads without fractionation; a low number of molecules can be presented on each bead by using beads that present a small number of functional groups or by using a large number of beads with a low concentration of the complex mixture.

Additionally, molecular biology techniques can be used to present a single or a small number of distinct species on beads. In this way, the in situ magnetic selection-dilution techniques, described herein, are particularly applicable to the study of proteomics. A set of magnetic beads can be generated to present the gene products of a cDNA library, then tested for their ability to interact with target species immobilized on a population(s) of colloids that may also bear auxiliary signaling elements. cDNA libraries are comprised of the fragments of genome that specifically code for proteins. cDNA libraries can be readily generated using standard techniques and are widely available from cell lines of interest. To facilitate the attachment of the proteins to beads or colloids, a cDNA library can be inserted, en mass or separately, into an affinity tag expression vector. For example, affinity tag vectors are used to produce histidine-tagged or glutathione-S-transferase (GST)-tagged proteins. Cells can then be transfected with the resultant plasmid DNAs. As those skilled in the art are aware, bacterial cells generally take up a single plasmid; in this way a pool of cDNA plasmids can be simultaneously transfected into cells, grown on agarose, and each colony will statistically contain a single species of transfected plasmid DNA. Colonies are picked and mini cultured, according to standard methods.

Cell cultures are then grown and induced to express the encoded proteins, according to standard techniques. To expedite the process, cell cultures (each representing a single clone) can be pooled together, grown and induced, enmass, to express the encoded proteins. The pooled proteins are then attached to a single bead. This means that when assayed with colloids presenting a target species, a bead that generated a positive signal simultaneously presents the interacting species as well as irrelevant species. Therefore, if pooled transfectants are used, the procedure can be repeated to determine which component of the bead-attached mixture actually interacted with the colloid-immobilized species, as follows. The bead-colloid mixtures can be subjected to standard analysis techniques, such as peptide micro sequencing, to determine which culture pool had been attached to that particular bead. The identification of a single protein from the mixture attached to the bead identifies the pool from which the transfectant was derived. Aliquots of the individual transfectants are reserved such that each transfectant can be separately grown and induced to express protein, which then is separately attached to a set of beads. The assay then is repeated to identify single interacting components.

Protein purification can be simplified by using magnetic beads that display binding partners of the affinity tag that was incorporated into the proteins. Alternatively, expressed proteins can be attached to magnetic beads via affinity tag interaction from a crude mixture or after standard purification.

A description of the analysis of interacting species, such as colloid-bead-immobilized species follows.

Magnetic beads that present species that interact with colloid-immobilized species, become coated with a colloid layer, due to the completion of the interaction between the species. These beads generate an electronic signal. After the in situ magnetic selection-dilution process, magnetic beads together with their attached colloids can be subjected to analysis techniques, such as MS, MALDI MS, peptide sequencing (s.a. Edman micro sequencing) and the like, which may also include enzymatic cleavage steps, to determine the identity of the putative interacting species. Immobilized proteins can be removed from the beads and colloids for analysis by a variety of methods, including but not limited to, competitive inhibition of the affinity tag-bead interaction, enzymatic digestion, acid elution and laser desorbtion. For example, proteins expressed with histidine-tags to facilitate attachment to surfaces presenting nitrilo tri-acetic acid/nickel (NTA-Ni) groups, can be released via the introduction of imidazole. Alternatively, proteins can be removed from supports using trypsin cleavage. Molecules can also be removed from particles by laser ionization desorption then directly input into an automated analysis system such as MS.

One method of the invention provides for massively parallel analyses of large numbers of putative interacting species. Such a system is especially useful for deciphering the protein interaction network of the gene products from the entire human genome.

In this case, cDNA libraries encoding the entire genome, a subset or a library of disease-associated genes are provided in distinct aliquots in separate locations. Each cDNA fragment is separately inserted into a protein expression vector. To facilitate attachment of the expressed protein to beads or colloidal particles, affinity tag vectors can be used. Cells are separately transfected with the plasmid DNA and protein expression is induced. At this point, proteins bearing an affinity tag are separately mixed with beads or colloids that bear a binding partner for the affinity tag. In this way, each particle will present a single protein species. For example, a first set of proteins, bearing histidine tags, is attached to a first set of magnetic beads bearing nitrilo tri-acetic acid (NTA) nickel moieties; NTA-Ni(II) binds stretches of histidines. A second set of proteins, bearing glutathione-S-transferase (GST) fusion moieties, is attached to gold colloids which present glutathione which is the binding partner of GST. Different particle types, i.e. beads verses colloids, need not bear different affinity tags. Each particle, however, bears a label that uniquely identifies the protein displayed on its surface. In a preferred embodiment, this label is a DNA sequence and gold colloids also display an electroactive signaling moiety.

According to methods of the invention described above, magnetic beads bearing a first protein set are mixed with gold colloids bearing a second protein set and an electroactive signaling moiety. The solution is placed over an electrode array. Beneath each pad of the electrode array is a separately controllable electromagnet. Proteins displayed on colloids are allowed to interact with proteins displayed on magnetic beads. Recall that if a protein attached to an electronic signaling colloid interacts with a protein on a magnetic bead, then the complex will transduce an electronic signal when recruited to the electrode. Magnetic beads alone are incapable of providing this signal. After some incubation period, all the electromagnetics are turned on in unison. Electromagnets, under pads that register a positive signal, are held "ON", while those that failed to generate a signal are released to release beads that did not interact with a colloid-immobilized partner. A port is opened and released beads are washed away. Fluid is introduced to the interaction chamber to dilute the remaining beads and electromagnets under pads that registered a positive are released. The process is repeated until one is assured that statistically, only beads decorated with signaling colloids remain.

Each magnetic bead and each colloid can bear a DNA strand that encodes the identity of the attached protein. At this point, pieces of single stranded, composite DNA are added to the interaction chamber. Each DNA strand is comprised of two parts: one end is complementary to a DNA sequence on a magnetic bead and the other end is complementary to a sequence on a colloid. All possible combinations of sequences on beads and colloids are represented. The DNA is allowed to freely interact with the bead-colloid complexes. Unbound DNA is washed out of the interaction chamber. DNA strands that simultaneously bind to a complementary sequence on a magnetic bead and a complementary sequence on a colloid represent "solutions" to the problem of which proteins interact with each other. Rather than perform peptide micro sequencing to reveal the identity of the interacting pairs, one merely elutes the bound DNA solutions and submits them to DNA sequencing. The sequence of each DNA strand will be the complement of the DNA code that identifies each protein.

Enzymes that digest single stranded DNA can be added to the solution after hybridization and rinsing to remove unbound portions of DNA. In this way, strands of DNA that bound to only one particle and not the other are not read as solutions. Enzymes having 3' and/or 5' exonuclease activity, such as *E. coli* DNA Pol I, which digest single stranded DNA from the ends, are preferred since they will not digest DNA nicks.

The length of DNA required to encrypt the protein set is a function of the number of distinct species in the set. Also, the length of the DNA "tag" is directly proportional to the number of mismatched bases that will be allowed without abolishing hybridization. For this reason, short DNA strands are preferred. Conditions such as temperature and salt concentration, along with the addition of chemicals like formamide, can also be optimized to ensure that only perfectly matched DNA will hybridize.

Alternatively, the magnetic bead-colloid complexes can be separately released from the interaction chamber, prior to the introduction of DNA "solution" strands, by sequential release of the electromagnets beneath each electrode pad. Each interacting complex can then be diverted to a separate location, where all possible DNA solutions are introduced. To relieve steric interference with DNA hybridization, the interacting protein partners can be dissociated from each particle and removed from the isolated location, prior to the introduction of DNA solution strands. DNA strands are allowed to simultaneously hybridize to beads and colloids in the absence of protein-protein interactions. Non-interacting DNA species are rinsed away, by for example pelleting the particles and removing the supernatant. Buffer suitable for the dissociation of DNA hybrids are added, particles pelleted and the DNA contained in the supernatant, which encodes the identity of the interacting proteins, are then sequenced by standard sequencing methods or by hybridization to DNA array chips.

To prevent proteins on magnetic beads from binding to each other before the introduction of proteins on colloids, magnetic beads can be added (en mass or separately) and magnetically drawn to the electrode array immediately. After an incubation period, electromagnets are released and incubated free in solution before the first round of selection and dilution.

Alternatively, components attached to beads and colloids can be pools of species.

The magnetic selection/dilution process described above will surely simplify analysis and enhance the accuracy of the experiment. However, it is not absolutely necessary in that the addition of DNA hybrid solutions alone will elucidate the identity of interacting pairs.

The signaling mechanism attached to the colloids need not be electronic or limited to the colloid. For example, the red color that the colloids impart when they agglomerate onto a surface can serve as the indicator that a species on a bead has interacted with a species on a colloid. In this case, the bead need not be magnetic. Alternatively, a fluorescent moiety can be attached to the colloids. Following an incubation period, the beads (magnetic or not) can be concentrated or pelleted so that the solution containing non-interacting colloids can be removed. Fluorescent beads are then separated from non-interacting beads and analyzed to reveal the identity of the interacting partners.

Although in the description above, "proteins" from a cDNA library are attached to the beads and colloids, the invention anticipates the attachment of a wide variety of putatively interacting species to the particles. These species may include, but are not limited to, chemical compounds, precursors of chemical compounds, reactive groups, protein complexes, nucleic acid-protein complexes, spores, cells, nucleic acids, peptides and drug candidates. These species can be attached to the colloids and beads via affinity tag interaction, non-specific binding, specific binding, or via covalent chemical coupling.

Additionally, the identifying tag attached to magnetic beads and colloids need not be nucleic acid based. Bead-colloid complexes can be separately released from the electrode pad and diverted to separate locations where the tags on the beads are deciphered. Identifying tags can include, but are not limited to, nucleic acid tags, radio frequency tags, fluorescent tags, fluorescence associated with a particle and chemical tags.

Various methods of the invention can be used to identify interaction motifs, rather than discrete binding partners. For this particular application, a first heterologous population of proteins is attached to a set of magnetic beads, and a second heterologous population of proteins is attached to a set colloids; each particle presents a single species. Following the magnetic selection-dilution process described herein, bead-colloid complexes are subjected to pool sequencing techniques to identify interaction motifs. Individual colloid-decorated beads are isolated. Each magnetic bead thereby presents a single species that is bound by a heterologous population of colloid-attached molecules. Interacting molecules are released from their particle supports by competitive inhibition of the affinity tag interaction. Interacting complexes are subjected to general enzymatic digestion by, for example, trypsin; interacting regions are protected from digestion. Complexes then are digested with N-terminal peptidase, which digests from the N-terminus to the point at which the interaction region or motif begins. After digestion, the interacting molecules are released from each other via acid elution. The mixture is then subjected to pool sequencing techniques, which typically involve Edman micro sequencing. The result of pool sequencing is that wherever there is a consensus motif, the identity of those amino acids is clear, while other regions appear as noise.

HPLC and similar techniques can be used to separate interacting species prior to sequencing analysis.

Alternatively, after colloid-decorated beads have been isolated, a first colloid-attached species can be released from their supports, via competitive inhibition of the affinity tag-colloid interaction, while a second set of proteins are allowed to remain bound to the beads. This can be accomplished by either having proteins bound to the beads via a different affinity tag interaction or by covalently coupling species to the beads. Enzymatic digestion then is performed while protein pairs remained bound to the beads. This procedure preferentially digests the first protein that is not directly attached to the bead, while protecting the second bead-attached species. Digestion products can be easily removed by concentrating the beads discarding the supernatant. The first species can then be eluted from its binding partner by acid elution or similar techniques. The supernatant, which contains the digested first species is then subjected to pool sequencing techniques to elucidate a consensus binding motif(s). The second species can be released from the bead and subjected to pool sequencing. Alternatively, the procedure can be repeated with the first species, or a consensus sequence derived from the first species, attached to the bead and the second species attached to the colloids.

Methods of the invention can be performed with: a single species presented on the colloids and many species attached to beads; many species attached to colloids and many species attached to beads; or many species attached to colloids and a single species attached to beads. Additionally, a mixed population of particles, each presenting a single distinct species can be used or a mixed population of particles presenting mixed species. In another aspect of the invention, magnetic beads that have been coated with a layer of interacting colloids are electromagnetically selected on the basis of differential mass. Alternatively, colloids can be modified to present not only a putative binding partner, but also a moiety that will impart differential electromagnetic properties when complexed with a magnetic bead(s). Magnetic beads decorated with these colloids can then be selected, separated and analyzed to reveal the identity of the particle-immobilized interacting partners.

In yet another aspect of the invention, the bead need not be magnetic. Colloid-bead complexes can be separated from unbound colloids by sedimentation, centrifugation or by physically removing beads that become decorated with colloids that may or may not present auxiliary signaling elements.

Similarly, particles that present putative binding partners with or without auxiliary signaling elements need not be colloidal. For example, molecules can be directly incorporated into liposomes along signaling moieties, such as ferrocene derivatives coupled to lipids. Alternatively, molecules can be attached, via affinity tag interaction, to liposomes that also incorporate binding partners for affinity tags.

Methods of the invention can be performed using a heterologous population of colloids that each present a single species or colloids that present more than one species. Species that can be attached to particles, as described herein, include but are not limited to proteins, domains or fragments of proteins, such as kringle domains, small molecules, natural products, and drugs.

Colloids that do not present an electroactive signaling element or that display additional signaling elements can also be used with aspects of this invention. For example, colloids can be derivatized to present electroactive as well as fluorescent moieties (including, by definition herein, phosphorescent moieties),. Each set of colloids can present a different color of fluorescence. FACS (fluorescence activated cell sorting) analysis can be used to sort hetero-particle complexes after magnetic selection, but prior to identifying molecular species attached to each bead. Colloid decorated magnetic beads can also be separated by electromagnetic methods. Additionally, colloids that do not bear an auxiliary signaling element can be used with aspects of the invention. These colloid-decorated beads can be identified visually, because the agglomeration of gold colloids onto particles colors them red. Additionally, nanoparticles that inherently fluoresce, for example as a function of their size, can also be used both to signal and to identify the surface-attached biomolecule.

One attribute of an aspect of the invention over the state of the art is that it enables the MULTIPLEXED identification and isolation of interacting species. This capability is especially useful in the field of proteomics because of the vast number of possible interaction between the gene products, which are the proteins. With the number of genes in the human genome now estimated to be about 40,000, determining interaction networks by sequential pair-wise testing will involve a minimum of $8 \times 10^8$ experiments. The isolation of interacting species attached to particle-like supports simplifies the analysis of interacting species, including the identification of interacting motifs. Additionally, the attachment of putative binding partners to solid supports enables the recovery and reuse of particles that presented species that did not interact.

EXAMPLE 1

Massively Parallel Analysis of Protein-Protein Interactions: Elucidating the Interaction Map of the Human Proteome The following prophetic example describes how to perform massively parallel analysis of protein-protein interactions, which is particularly useful when proteins are as yet uncharacterized. Here, this method is used to elucidate the protein interaction map of the human proteome. A subset of, or the entire set of, proteins of the proteome is expressed with affinity tags to facilitate attachment of the expressed protein to sets of particles. Particle-immobilized proteins are pooled together and allowed to interact. Interacting pairs are selected from the pooled mixture by a reiterative magnetic selection/dilution process. Following the selection/dilution process, the identity of interacting partners is determined. The selection step reduces the complexity of the problem by eliminating the need to analyze non-interacting proteins.

Figure 6:
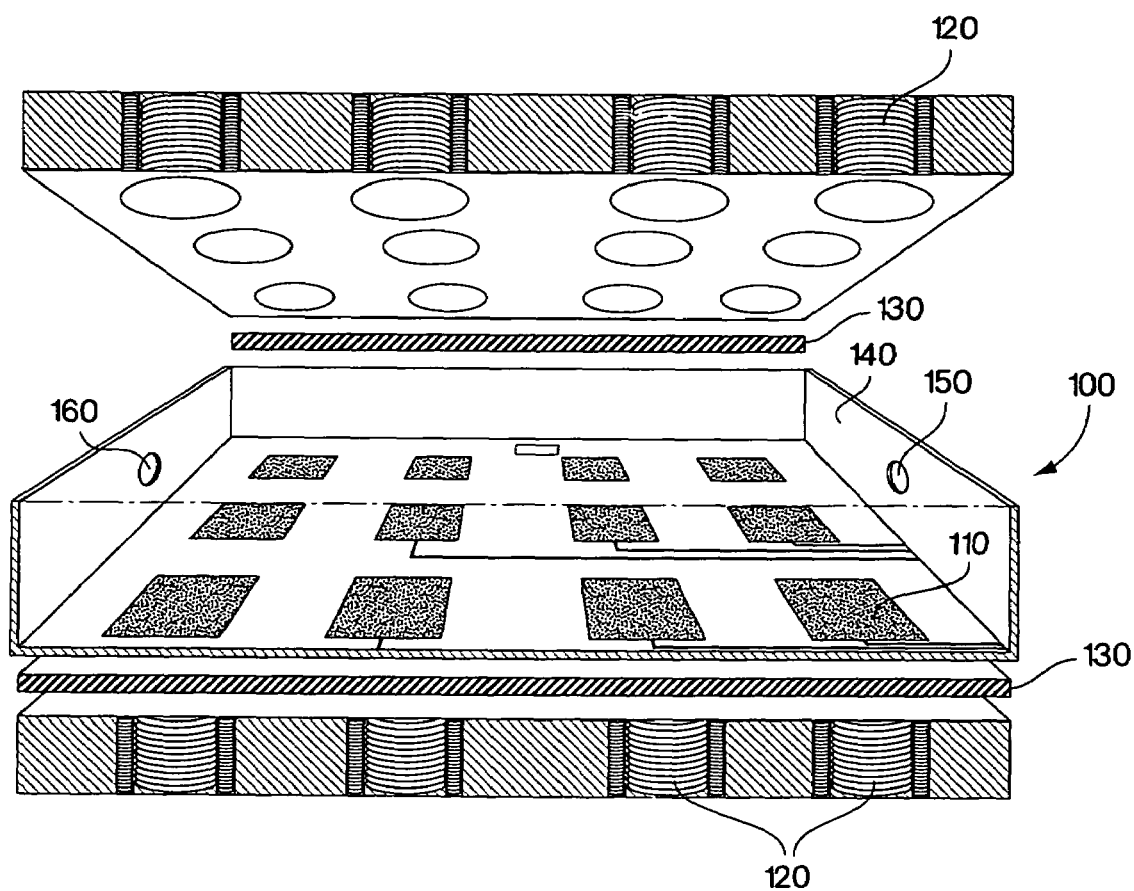
FIG. 6 illustrates a multiplexing apparatus for applying and releasing a magnetic force at multiple locations on a continuous surface.

Proteins and their encoding DNA molecules are indirectly connected to each other by co-immobilizing both on a common particle or bead, wherein each particle (or bead) presents a single protein species and its encoding DNA. Connecting the expressed protein to its encoding DNA expedites the identification of each set of interacting proteins after the selection/dilution process. Each protein and its encoding DNA are immobilized on two different kinds of particles: a recruitable particle and a signaling particle. The sizes of the particles are also different such that smaller signaling particles can form satellites around each larger recruitable particle. In this example, each protein and its encoding DNA are immobilized on a single 4-10 micron magnetic bead as well as on a multitude of fluid suspendable nanoparticles, that are 4-40 nm in diameter and bear electroactive signaling entities. When a first species on a magnetic bead biologically interacts with a second species on a signaling nanoparticle, the recruitable particle becomes "connected" to the signaling particle. These hetero-particle-complexes are then magnetically recruited to a sensing electrode (see FIG. 6), where they can deliver a signal, such as an electronic or electrochemical signal. To facilitate multiplexed analysis, the particles are magnetically attracted to an electrode array that has a number of individually addressable electrode pads. Beneath each electrode pad is an individually controllable electromagnet, such that the magnetic field above each pad can be selectively turned off and on. However, magnetic particles that are not connected to signaling particles, which cannot deliver a signal, may also be recruited to the same electrode pad that delivers a positive signal. These non-signaling magnetic beads are electromagnetically released from the pad and washed out of the interaction reservoir. Signaling nanoparticles that do not interact with species on magnetic particles remain in a homogeneous suspension and do not deliver a signal but are also washed out of the interaction reservoir. Both of these purging functions are accomplished by maintaining the magnetic fields beneath electrode pads that deliver a positive signal, to retain interacting complexes, while the magnetic fields beneath pads that do not deliver a positive signal are driven to zero to release non-interacting magnetic beads. A port 150 (FIG. 6) is opened and fluid is washed out of the interaction reservoir carrying away non-interacting magnetic beads and non-interacting nanoparticles. The port is closed, all magnetic fields are driven to zero and more buffer is added through a second port 160 along with mechanical agitation to resuspend and redistribute the particles. All the magnetic fields beneath all the electrode pads are turned on again and the selection/dilution process is repeated until, statistically, each pad that delivers a positive signal contains a single magnetic bead bound to a multitude of signaling nanoparticles.

To determine the identity of interacting proteins, an array of magnetic pins, whose dimensions correspond to that of the electrode array is juxtaposed over the electrode array and the magnetic fields beneath the entire electrode array are driven to zero such that each magnetic pin captures a single hetero-particle complex. The loaded pin array is dipped into a multi-well plate, of compatible dimensions, each well of which is filled with solution containing DNA amplification reagents. The respective encoding DNA sequences (immobilized on the nanoparticles and the bead) are amplified by PCR or similar technique and sequenced to reveal the identity of each set of interacting proteins. Individual aspects of the experiment are detailed below.

Preparation of Proteins

A DNA sequence that encodes each protein member of the proteome is inserted into a bacterial protein expression vector. The expression vector carries an affinity tag, $(His)_6$ in this case, tandem repeats of Ga14 consensus sequences, and 2 sequences that flank the protein identification sequence, to which PCR primers can bind. The histidine-tag facilitates the attachment of the expressed protein to the particle. The Ga14 consensus sequences act to tether the encoding DNA to the particle via the interaction between the recognition motif and a particle-immobilized yeast DNA binding domain, which in this case is a GST-Ga14 fusion protein. The DNA binding domain of Ga14 (aa' 1-100) binds to the consensus sequence CGGattAgAagcCgCCGAG and the GST binds to a glutathione moiety on the particle. Proteins are separately expressed in a cell-free translation system to reduce the abundance of irrelevant proteins and cell debris. Following protein expression, each expression mixture contains the encoding DNA and the expressed protein. Each protein expression mixture is divided into 2 aliquots. A single magnetic bead (4-10 microns in diameter) is added to a first aliquot and a quantity of NTA-glutathione-SAM-coated nanoparticles is added to a second aliquot. Particles are pelleted and washed to remove protein that is not particle-bound. Particles and beads are pooled together in subsets of 1000 species per pool and subjected to magnetic selection/dilution and electrochemical analysis. In this manner, unidentified proteins can be bound to the same bead or particle that also binds the corresponding encoding DNA.

Preparation of Nanoparticles

Gold nanoparticles (diameter=4-25 nm) are derivatized with heterologous self-assembled monolayers (SAMs) that present:
a) NTA (nitrilo tri-acetic acid)-$Ni^{++}$ that captures histidine-tagged proteins;
b) glutathione that binds to glutathione-S-transferase (GST) fusion proteins;
c) octamethyl ferrocene, which is a redox active moiety that can deliver an electronic or electrochemical signal;
d) carboxylates to prevent particle aggregation; and
e) tri-ethylene glycol to resist non-specific adsorption. Virtually any biological species can be immobilized on a colloid.

Electrochemical Analysis

A model 630 electrochemical analyzer from CH Instruments (Austin, Tex.) is used to detect interactions between species immobilized on magnetic beads and species immobilized on colloids that also bear redox active metals. The instrument is modified to facilitate multiplexed detection. In this case, the redox active metals are ferrocene derivatives. Pads of the electrode array are individually addressable and act as the working electrode. In this case, the pads are gold-coated and derivatized with conductive self-assembled monolayers. A Ag vs. Ag/Cl reference electrode is used with a Pt auxiliary. Electrodes are scanned using Alternating Current Voltammetry (ACV) with a 25 mV overpotential at a frequency of 10 Hz.

Design of Electrode Array Sandwiched between Individually Addressable Electromagnets Electrode arrays 100 (FIG. 6) having 300-500 electrode pads 110 are constructed by plating gold over $Ni^{++}$. Electrode pads are 50-500 microns on edge and are sandwiched between sets of individually addressable Helmholtz electromagnets 120 such that a magnetic field gradient can be generated to recruit, then hold magnetic beads at the pad surface (see FIG. 6). The direction of the current is reversed to drive the magnetic field to zero when it is desirable to release magnetic beads from the surface to wash away or redistribute. To ensure that the interaction reservoir is thermally isolated from the electromagnet arrays so that heat does not denature proteins in solution, a layer of insulative material 130 is placed between the electromagnets and the interaction reservoir 140.

Calculation of Protein Sets and Electrode Pad Number

To generate the protein interaction map of the entire proteome, one needs to divide the proteome into subsets, which are then tested for interaction with every other subset. Assuming that there are about 50,000 proteins of interest, the proteome is divided into 50 sets of 1000 proteins each. Each group of 1000 proteins is then tested for interaction with every other group of 1000, resulting in 50×50 matrix or 2500 separate experiments. The number of proteins in each subset determines the number of electrode pads in each array. If we assume that each protein has a single binding partner, then each protein has a 1/50 chance of finding that partner when tested for interaction with one of the 50 subsets of proteins. However, each protein probably has on average 5 relevant binding partners, increasing the probability of finding a binding partner within a subset to 1/10. That means that for 2000 proteins in one pooled interaction mix, 200 will deliver a positive signal, which implies that the electrode array should have 300-500 pads. Low-level signals from non-specific binding events are minimal because of competitive inhibition by relevant binders. However, the occurrence of false positives is minimized when a signal threshold is set, wherein signals below the threshold are counted as negatives. Relative affinities are determined by comparison of the degree of interaction of a first binding species and a second binding species with a third target protein to which the first and second bind.

EXAMPLE 2

Determining the Binding Partners of a Single Target Protein with a Large Pool of Candidate Binding Partners This prophetic example describes how to identify proteins, from a large pool of putative binding partners, which interact with a single target protein. Proteins from the large pool are prepared as described above in Example 1, and immobilized only on signaling nanoparticles. The target protein is immobilized on a set of magnetic beads. Because the identity of the target protein is known, it is not necessary to co-immobilize its encoding DNA. Interacting partners are selected by electrochemical analysis as described above.

EXAMPLE 3

Selection of Interacting Protein Partners by FACS Analysis

This example describes how to identify the binding partners of a single target protein. The target protein is immobilized on a set of beads that are 4-25 microns in diameter. Putative binding partners, which may be prepared as described above or generated from a cDNA library, are co-immobilized along with their encoding DNA onto nanoparticles that bear fluorescent signaling moieties. When a bead-immobilized protein interacts with a species immobilized on nanoparticles, the bead becomes decorated with fluorescent nanoparticles and can be isolated by FACS (fluorescent activated cell sorting) analysis after which the attached DNA of each interacting species is sequenced to identify the binding partners.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described. In the claims the words "including", "carrying", "having", and the like mean, as "comprising", including but not limited to.

What is claimed is:

1. A method of magnetically manipulating a chemical or biological agent comprising:
   providing a plurality of magnetic beads or magnetic particles each carrying a chemical or biological agent immobilized relative thereto;
   exposing the beads or the particles to a plurality of nanoparticles each carrying a potential binding partner of the chemical or biological agent to allow the nanoparticles to bind to some of the magnetic beads or magnetic particles via chemical or biological agent/binding partner interaction thereby forming a first article;
   magnetically drawing the magnetic beads or the magnetic particles to a plurality of predetermined locations at a surface;
   determining first surface locations at which the first article has been drawn and second surface locations substantially free of nanoparticles; and
   selectively magnetically releasing magnetic beads or magnetic particles from the second surface locations while holding magnetic beads or magnetic particles of the first article at the first surface locations.

2. A method as in claim 1, wherein the nanoparticle is a signaling entity.

3. A method as in claim 1, wherein the nanoparticle comprises a signaling entity immobilized relative thereto.

4. A method as in claim 3, wherein the signaling entity is a metallocene fastened to the nanoparticle.

5. A method as in claim 4, wherein each of the surface areas comprises an electrode, and an electromagnet is associated with each of the first and second surface areas, positioned to draw the first article to the first surface area and the magnetic bead or magnetic particle to the second surface area, respectively.

6. A method as in claim 4, wherein the metallocene is ferrocene.

7. A method as in claim 1, wherein the biological or chemical agent is a candidate drug.

8. A method as in claim 1, wherein the drawing step is carried out in the presence of a candidate drug, and the biological or chemical agent is a potential target of the candidate drug.

9. A method as in claim 1, further comprising removing magnetic beads or magnetic particles released from the vicinity of the second surface locations; and
   repeating one or more times the steps of magnetically drawing, determining, and releasing.

10. A method as in claim 9, comprising detecting the presence of nanoparticles at surface locations visually.

11. A method as in claim 9, comprising detecting the presence of nanoparticles at surface locations by electromagnetically stimulating a metallocene linked to the nanoparticles.

12. A method as in claim 1, further comprising:
    removing magnetic beads or magnetic particles released from the vicinity of the first and second surface locations;
    releasing magnetic beads or magnetic particles from the first surface locations; and
    repeating one or more times the steps of magnetically drawing; determining, and releasing.

13. A method as in claim 12, further comprising, prior to the repeating step:
    adding fluid to dilute particles released from the first surface locations.

14. A method as in claim 12, further comprising identifying at least one first chemical or biological agent.

15. A method as in claim 1, comprising detecting the presence of nanoparticles at surface locations by electromagnetically stimulating a metallocene linked to the nanoparticles.

16. A method as in claim 1, wherein the first article further comprises a DNA sequence immobilized thereto on the magnetic bead or the magnetic particle which identifies the biological or chemical agent of the first article, the method further comprising identifying the biological or chemical agent of the first article by identifying the DNA sequence.

17. A method as in claim 16, comprising first selectively magnetically releasing the magnetic beads or the magnetic particles from the second location while holding the first article at the first location, and then identifying the biological or chemical agent of the first article by identifying the DNA sequence.

18. A method as in claim 1, further comprising providing at least one magnetic bead or magnetic particle held at a first surface location according to the method, and identifying at least one chemical or biological agent carried by the at least one magnetic bead or magnetic particle by identifying a DNA sequence immobilized relative to the magnetic bead or magnetic particle.

19. A method as in claim 1, further comprising providing at least one magnetic bead or magnetic particle held at a first surface location according to the method, the magnetic bead or magnetic particle immobilized relative to a nanoparticle, and identifying at least one binding partner of the chemical or biological agent carried by the at least one magnetic bead or magnetic particle by identifying a DNA sequence immobilized relative to the nanoparticle.

* * * * *